United States Patent [19]

Saringer

[11] Patent Number: 5,628,769
[45] Date of Patent: May 13, 1997

[54] METHOD AND DEVICES FOR PRODUCING SOMATOSENSORY STIMULATION USING TEMPERATURE

[75] Inventor: John H. Saringer, Markham, Canada

[73] Assignee: Saringer Research, Inc., Markham, Canada

[21] Appl. No.: 316,352

[22] Filed: Sep. 30, 1994

[51] Int. Cl.⁶ .................................................. A61F 7/02
[52] U.S. Cl. ................................................................ 607/98
[58] Field of Search ............................ 607/96–98, 104, 607/108–112

[56] References Cited

U.S. PATENT DOCUMENTS

| | | |
|---|---|---|
| 3,132,688 | 5/1964 | Nowak . |
| 3,268,895 | 8/1966 | Okuhara . |
| 3,888,259 | 6/1975 | Milley . |
| 3,967,627 | 7/1976 | Brown . |
| 4,094,357 | 6/1978 | Sgroi . |
| 4,170,988 | 10/1979 | Sauder . |
| 4,280,499 | 7/1981 | Sguazzi . |
| 4,425,917 | 1/1984 | Kuznetz . |
| 4,459,468 | 7/1984 | Bailey . |
| 4,523,594 | 6/1985 | Kuznetz . |
| 4,585,002 | 4/1986 | Kissin . |
| 4,640,284 | 2/1987 | Ruderian . |
| 4,781,193 | 11/1988 | Pagden . |
| 4,846,176 | 7/1989 | Golden . |
| 4,860,748 | 8/1989 | Churco . |
| 4,915,108 | 4/1990 | Sun . |
| 4,962,761 | 10/1990 | Golden . |
| 5,097,828 | 3/1992 | Deutsch . |
| 5,174,285 | 12/1992 | Fontenot . |
| 5,209,227 | 5/1993 | Deutsch . |
| 5,269,369 | 12/1993 | Faghri . |
| 5,314,456 | 5/1994 | Cohen . |

FOREIGN PATENT DOCUMENTS

| | | |
|---|---|---|
| 1274836 | 8/1968 | Germany . |
| WO91/10414 | 7/1991 | WIPO . |

*Primary Examiner*—Angela D. Sykes
*Attorney, Agent, or Firm*—Lynn C. Schumacher; Hill & Schumacher

[57] ABSTRACT

The present invention provides a method of abatement of pain using somatosensory stimulation and devices for implementing the method. The method involves application of spatially modulated temperature differences to the skin in the vicinity of pain. The application of a spatial temperature difference produces a large sensory stimulus along neural pathways the same as or adjacent to those transmitting the signals giving rise to the sensation of pain. This acts to cause the brain to block sensation from the affected area thereby alleviating the pain and the brain has no built in method of adapting or habituating to this type of sensory input. The temperature differential applied is up to 40°–45° C. with the high temperature maintained at or below 45° C. and the low temperature at or above 0° C. to prevent tissue damage. Several devices are disclosed for implementing the method with one being a hand-held device using a thermoelectric unit to both heat and cool adjacent parts of a surface which is in contact with the skin. Another larger device uses a thermoelectric unit disposed between two water pumps each of which pumps water to different sections of a flexible water bag which is strapped to the affected area of the user. Water pumped over one side of the thermoelectric unit is heated and water pumped over the other side is cooled.

7 Claims, 8 Drawing Sheets

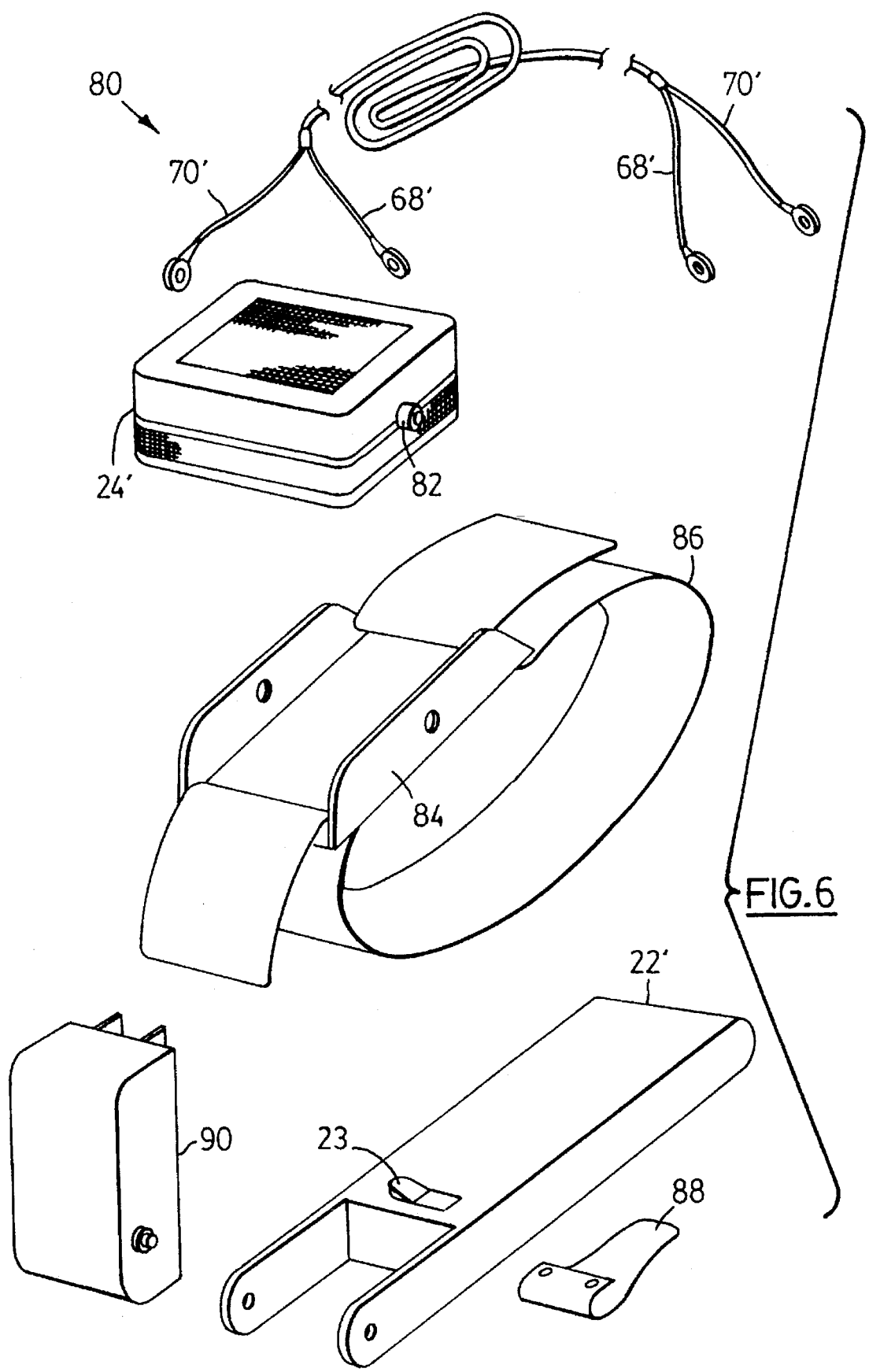

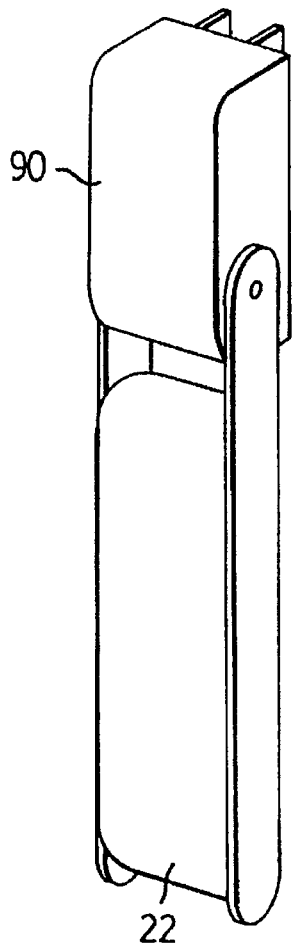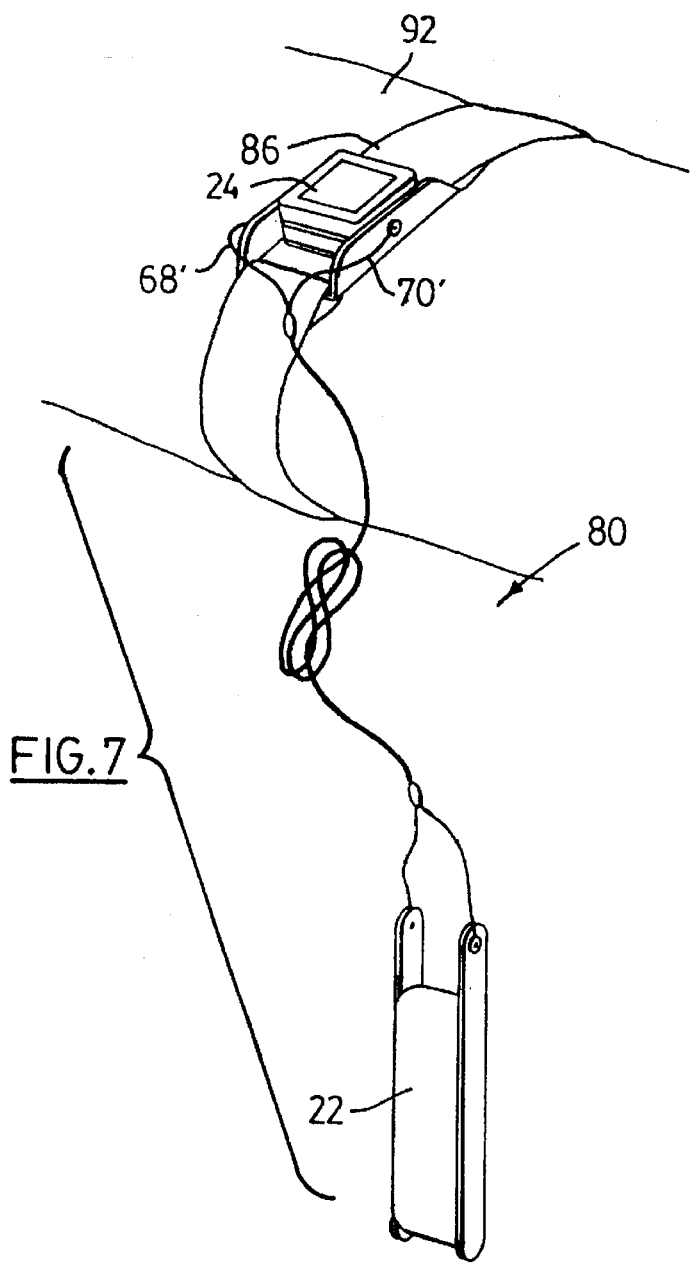

METHOD AND DEVICES FOR PRODUCING SOMATOSENSORY STIMULATION USING TEMPERATURE

FIELD OF THE INVENTION

The present invention relates to a method and devices for producing somatosensory stimulation for alleviating pain. More particularly the invention relates to a method of alleviating pain by simultaneously heating and cooling adjacent skin areas in the vicinity of pain and to devices for implementing the method.

BACKGROUND OF THE INVENTION

Pain abatement research is a major area of study which goes hand-in-hand with pain research itself. In many cases pain is a symptom of an underlying malady so the presence and nature of the pain in these cases is sometimes essential in aiding awareness and the diagnosis of the underlying illness. The abatement of pain has traditionally been effected using various external and internal treatments. Examples of external treatment include acupuncture, electro-shock treatment using transcutaneous electrical nerve stimulation (TENS), use of temperature such as application of hot or cold packs or topical application of cooling or heating formulations. Examples of internal, invasive treatments include drug treatments by oral administration or injection or injection of freezing agents. Where feasible, the external physical methods of alleviating pain are preferable over the invasive, internal techniques for obvious reasons.

The application of hot or cold to localized pain such as muscle or tendon pain to reduce swelling has a long history. There are many devices for heating or cooling parts of the body. Hot water bottles and ice or cold packs are among the oldest and simplest devices for applying heat and cooling respectively. Another type of device is the heating blanket that uses electrical resistive heaters for heating. U.S. Pat. No. 4,094,357 discloses a heat transfer blanket which uses heat pipes coupled to heating/cooling systems. U.S. Pat. No. 5,269,369 teaches a body suit which utilizes a system of heat pipes to redistribute body heat for heating or cooling the person wearing the suit.

U.S. Pat. Nos. 4,459,468 and 4,962,761 disclose fluid circulation systems for use with thermal bandages, pads or blankets. A drawback to these circulations systems is that they are quite bulky and awkward since they use large fluid pumps between the heat exchanger and the blanket or pad being heated or cooled. Other systems employ condensers, refrigerants and evaporator coils which are also bulky, awkward and of limited mobility.

The use of heating or cooling to alleviate certain types of pain by stimulating or constricting blood flow is well known. U.S. Pat. No. 5,314,456 issued to Cohen discloses a heating pad for relief of headache-related back, neck and head pain designed to induce venous constriction and enlargement to alter blood flow in the head to relieve headaches. Similar devices are disclosed in U.S. Pat. No. 4,061,898 directed to a heating cap for alleviating headaches and U.S. Pat. No. 4,781,193 which is directed to a headache treatment device which specifically heats the top of a patient's head using a resistively heated cap and cools a portion of the head around the patient's temples and brow using a cooled headband. A conventional refrigeration cycle uses a bulky and heavy compressor and condenser to cool the head band.

Temporal temperature modulation techniques have been developed wherein the applied temperature is switched between hot and cold. For example, U.S. Pat. No. 4,585,002 discloses a method and apparatus for alleviating pain through somatosensory stimulation achieved by frequent alternating temperature stimulation of the skin adjacent to the area of pain. This patent teaches that the habituation to heat and cold can be overcome by cycling one after the other to cause a dynamic temperature sensation more intense than achievable with either hot or cold individually. The frequency of the temperature change from hot to cold or vice versa is several times per minute which is observed to induce the maximal dynamic phase of the thermoreceptors in tissue. An improvement over U.S. Pat. No. 4,585,002 is disclosed in U.S. Pat. No. 4,860,748 which uses a thermal pattern generator to produce a variety of thermal wave patterns of hot and cold but with temperature switching frequencies of the order of a minute, greater than the switching times disclosed in '002. These devices use Peltier thermoelectric units so that the temperature depends on the polarity of the current through the thermoelectric unit.

It is believed that the mechanism of pain relief achieved through thermal somatosensory stimulation is related to the heating or cooling of the skin in the vicinity of the pain thereby swamping or overwhelming the pain stimuli. Briefly, it is believed that pain is a sensation that can be overwhelmed by other intense stimuli from the same or adjacent neural pathways. The brain responds to the intense stimulus by blocking it which has the beneficial effect of also blocking the sensation of pain. As disclosed in the publication "The Challenge of Pain" by Melzak et al., sensory modulation is believed to have a significant impact on the sensation of pain. Many forms of pain can be overwhelmed or obscured by other intense stimuli from the same or adjacent neural pathways wherein the brain responds to such intense stimuli by blocking the stimulus and concurrently the sensation of pain.

Heat and cold are among the most intense stimuli that can be safely applied to the human body within an appropriate temperature range without causing permanent injury or damage. Skin can withstand temperatures in the range from about 0° C. to 45°–50° C. for extended periods of time without causing permanent damage or injury. While many prior art methods of alleviating pain teach application of heat or cold, these methods involve applying one or the other alone or alternating heat and cold temporally on the effected area. Application of heat or cold alone is accompanied by adaption which decreases the efficacy of the technique. In other words the maximum benefit occurs during the initial period of heating or cooling and drops off once the body adapts to the heat or cold.

A drawback to temporal temperature modulation techniques is that a significant fraction of the duty cycle is required for the skin temperature to reach the temperature of the device so the maximum sensory stimulus is not achieved. Further, among devices that employ heat and/or cold for somatosensory stimulation to block pain, adaptation or habituation to the sensation limits the effectiveness of the treatments. In all these cases the treatments are similar to naturally occurring phenomena and hence the body has built in methods of adaptation.

It would therefore be advantageous to provide a method of alleviating pain which provides a higher degree of somatosensory stimulation than taught by the prior art in which the limitations of adaptation are reduced.

SUMMARY OF THE INVENTION

It is an object of the present invention to provide a method for alleviating pain using somatosensory stimulation achieved by applying heat and cold simultaneously to adjacent skin areas in the vicinity of the pain on any part of a patient's body.

It is also an object of the present invention to provide devices which can heat and cool adjacent skin areas simultaneously.

The present invention provides enhanced somatosensory stimulation by concurrently heating and cooling adjacent skin areas in the vicinity of pain to a large but safe temperature differential. Large spatially modulated temperature differences within confined areas on the skin surface, on the other hand, are totally artificial and accordingly the brain has no mechanism to habituate or adapt other than through total suppression of all signals from stimuli, including pain, from the affected area. Hence, the limitations inherent in sequential heat or cold treatments as a result of habituation and adaptation responses of the brain are reduced. It is believed that the resulting somatosensory stimulation is superior to that produced by temporal thermal modulation since the same neural pathways are simultaneously flooded with hot and cold stimulation so the resulting brain response to habituate to the heat causes enhancement of the sensation of cold and conversely habituation to cold serves to increase the sensation of heat, hence any brain response to adapt to one sensation is self-defeating since it causes increased sensitivity to the other. This results in a second order or meta response being triggered in which all sensations from the area, including any pain present, is effectively suppressed. Therefore, assuming that first order adaptation to hot and cold is effectively blocked, then this meta response is triggered.

In one aspect of the invention the method of alleviating pain using temperature comprises producing somatosensory stimulation in patients having a pain locus on their body which is sensed in their brain by way of signals transmitted along neural pathways from the pain locus using temperature for pain abatement. The method comprises the steps of simultaneously heating a first area and cooling a second area of the patient's skin adjacent to the neural pathways to stimulate additional signals of sensed heating and cooling along the neural pathways extending from the pain locus to the patient's brain.

In another aspect of the invention there is provided a method of producing somatosensory stimulation in a patient having a pain locus and neural pathways transmitting pain signals to the patient's brain using temperature for pain abatement. The method comprises simultaneously heating and cooling adjacent skin areas in the vicinity of the pain so that signals of heat and cold are transmitted along said neural pathways to the patient's brain. The temperature of the heated skin area no higher than about 45° C. and the temperature of the cooled skin area is no less than about 0° C.

In another aspect of the invention there is provided a device for simultaneously heating and cooling adjacent skin areas. The device comprises a member adapted to be applied to the skin which includes at least a first section which can be heated and at least a second section which can be cooled with the first and second sections being adjacent to each other for heating and cooling adjacent skin areas. The device includes means for simultaneously heating the first section to at most 45° C. and cooling the second section to 0° C. or higher.

The present invention also provides a fluid pump comprising a housing having an open end portion and one of either a heat source and heat sink attached to said housing at the open end portion. The fluid pump includes a motor with an impeller operably coupled thereto for rotation with the motor and impeller located in the housing with the impeller adjacent to said one of either a heat source and heat sink. The housing provided with a fluid inlet for admitting heat transfer fluid into the housing. The housing includes at least one fluid recirculation outlet and at least one fluid recirculation inlet, whereby rotation of the impeller forces the heat transfer fluid over said one of either a heat source and heat sink through the fluid outlet.

BRIEF DESCRIPTION OF THE DRAWINGS

The following is a description, by way of example only, of the method of, and various devices for inducing somatosensory stimulation forming the present invention, reference being had to the accompanying drawings, in which:

FIG. 2 is a perspective view of an alternative embodiment of the device for applying temperature differentials to the skin;

FIG. 6 is a disassembled perspective view of a alternative embodiment of the somatosensory stimulation device of the present invention;

FIG. 7 is a perspective view of the embodiment of the device of FIG. 6 in use;

FIG. 8 is a perspective view of the device of FIG. 6 assembled for recharging of the power supply;

DETAILED DESCRIPTION OF THE INVENTION

Figure 1:
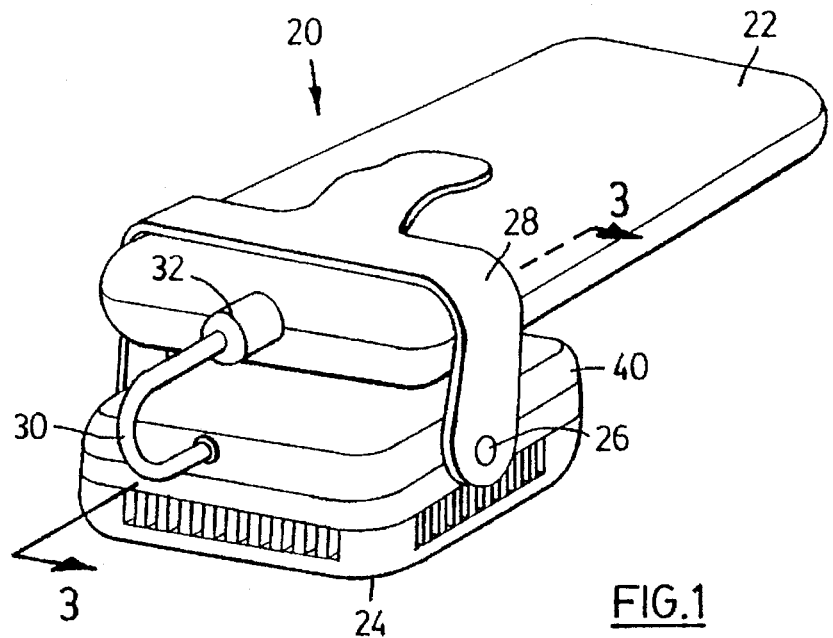
FIG. 1 is a perspective view of a somatosensory stimulation device for applying temperature differential to adjacent skin areas constructed in accordance with the present invention.

Referring first to FIG. 1 a portable device for alleviating pain using somatosensory stimulation is shown generally at 20. Device 20 comprises a handle 22 to which a head 24 is pivotally attached at 26 using a bracket 28. Handle 22 encloses a power supply such as a rechargeable battery (not shown). Electrical connection to head 24 is made by wire 30 from the head to a plug 32 which in turn is electrically connected to the power supply. An on-off switch (not shown) is located in handle 22 for turning the power to head 24 on and off.

FIG. 2 shows an alternative embodiment of a hand-held device 200 similar to device 20. Head portion 204' has a hemispherical shape which functions in essentially the same way as head 24 of FIG. 1.

Figure 3:
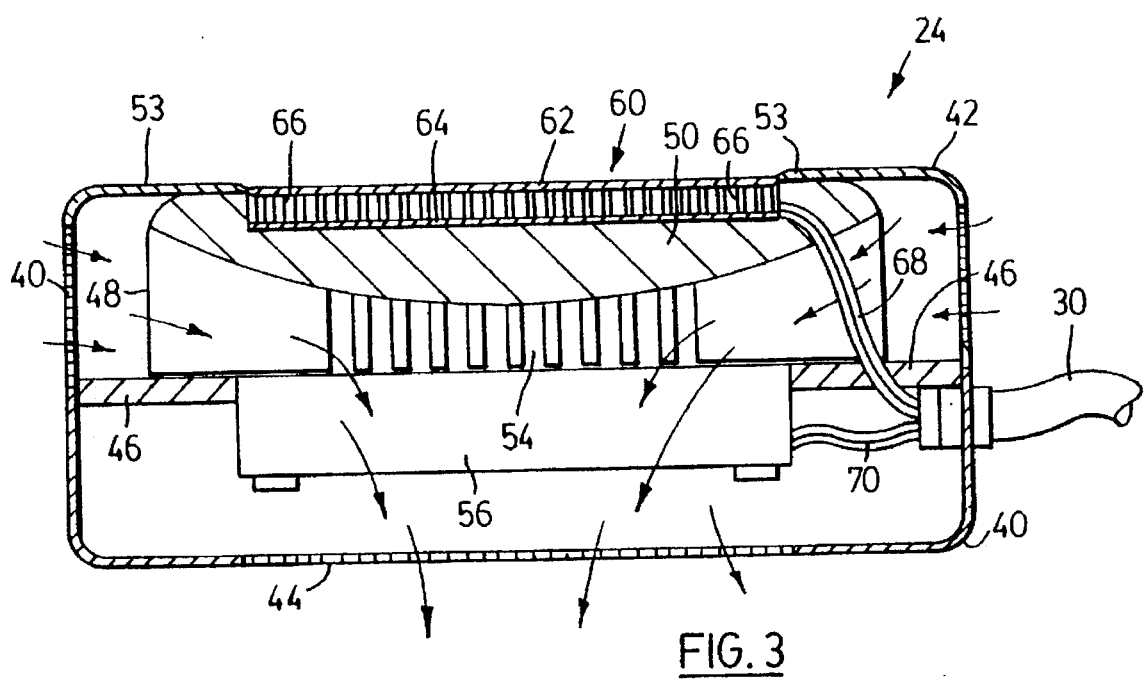
FIG. 3 is a cross-sectional view along the line 3—3 of FIG. 1.
Figure 4:
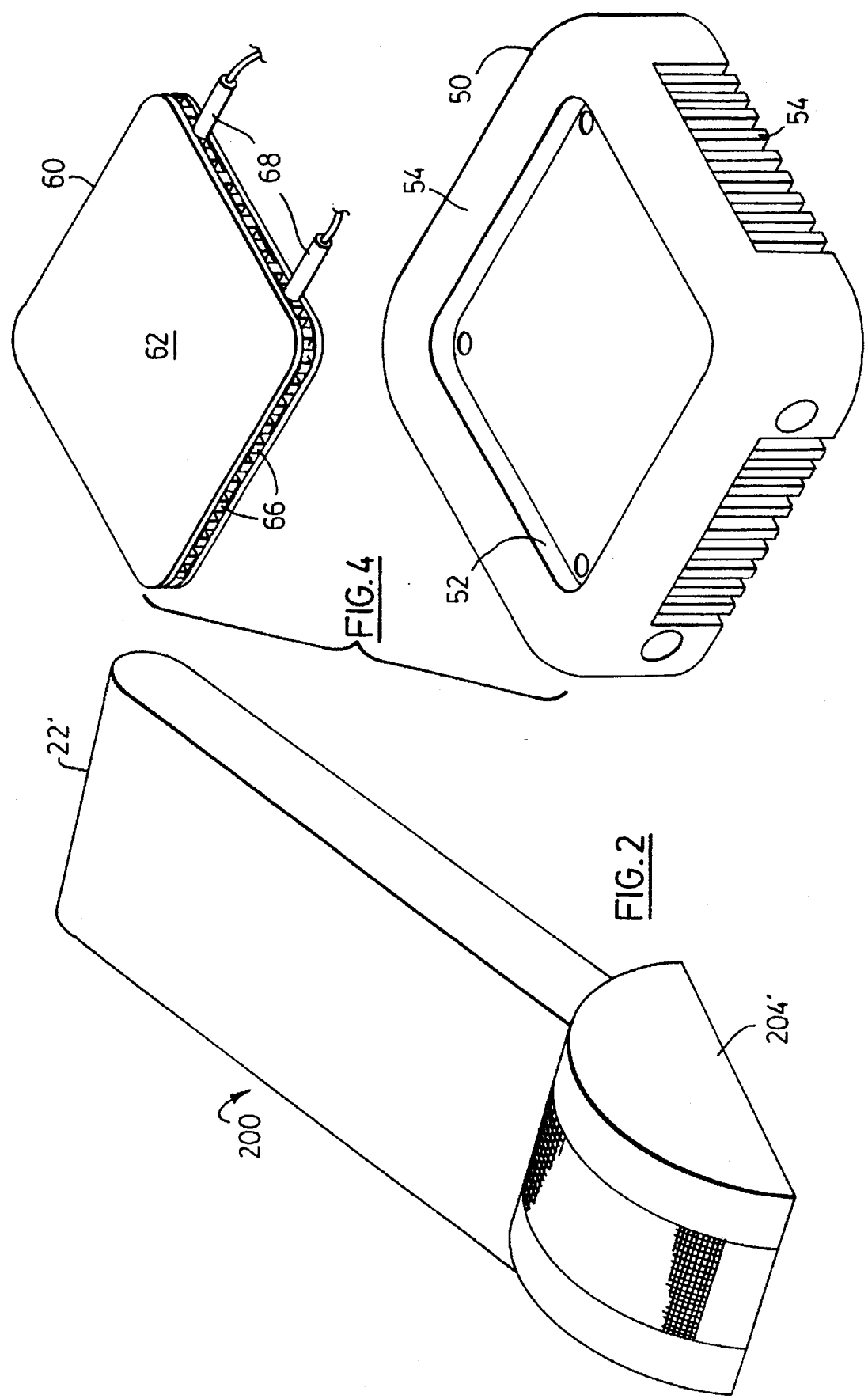
FIG. 4 is an exploded perspective view of a portion of the device of FIGS. 1 and 3.
Figure 5:
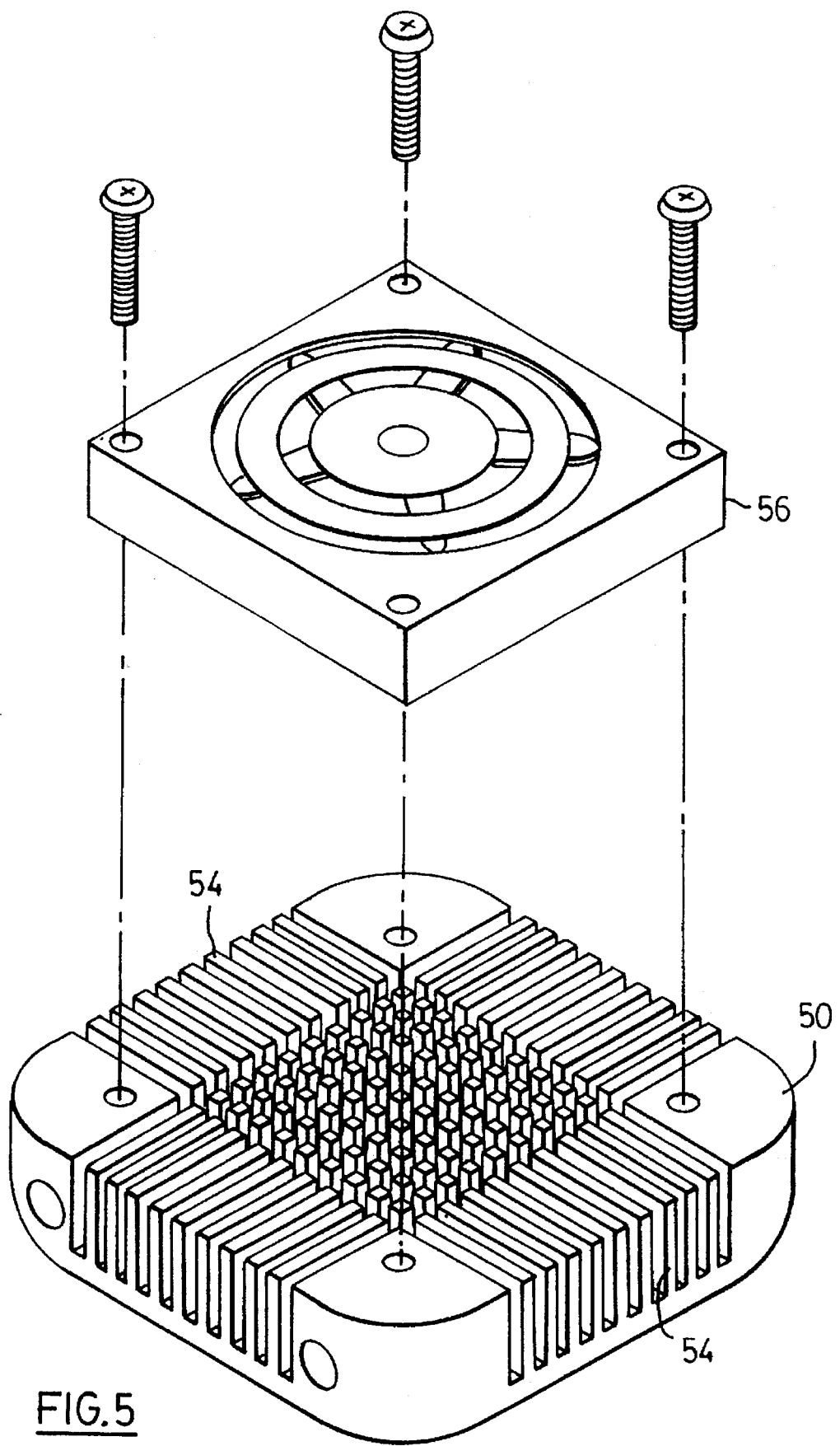
FIG. 5 is an exploded perspective view of a portion of the device of FIGS. 1 and 3.

Referring now to FIGS. 3–5, the components comprising head 24 are more clearly visible. Referring specifically to FIG. 3, head 24 incudes a housing 40 having a front face 42 and a back face 44 and is provided with webbing 46 spaced therebetween. An aluminum block 48 is located within housing 40 between webbing 46 and front face 42. Aluminum block 48 comprises a solid section 50 containing a well 52 (best seen in FIG. 4) with a planar perimeter 53 enclosing the well. Block 48 includes a finned section 54 adjacent to solid section 50. Finned section 54 is located adjacent to a fan 56 (FIG. 5) which when assembled is attached to webbing 46 on the interior of housing 40 as shown in FIG. 3.

Referring again to FIG. 3, a thermoelectric unit 60 is located in recess 52 and is provided with a front face 62 and a back face 64. Back face 64 is in thermal contact with section 50 of block 48. The finned section 54 on block 48 in conjunction with fan 56 provide heat dissipation of excess heat generated by thermoelectric unit 60. Power from the power supply is fed to thermoelectric unit 60 and fan 56 through wires 68 and 70 respectively.

Thermoelectric unit 60 utilizes the Peltier effect so that when an electric current is passed into unit 60 through wires 68 one side of unit 60 is heated up and the other side is cooled. In the configuration shown in FIG. 3, side 64 is heated and side 62 is cooled. A typical thermoelectric unit 60 is shown as part of FIG. 4 and is a Melcor CP1.0-127-06L or related model of dimensions 30×30 mm with an array of 127 thermoelectric elements 66 arranged in a rectangular pattern with power ratings between 5 to 25 Watts. Planar perimeter 53 extending around thermoelectric unit 60 is heated by surface 64 and surface 62 of the unit is cooled when the power is turned on. Fan 56 may for example be a 5 CFM 40×40×10 mm fan as used for cooling central processing units in personal computers. The arrows in FIG. 3 illustrate the flow path for air drawn by fan 56 through the finned section 54 of block 48 for dissipation of heat. This is the preferred arrangement in order to provide the most efficient heat dissipation in the device.

The power to thermoelectric unit 60 is controlled so that surface 53 does not exceed 45° to 50° C. and surface 62 does not drop below about 0° C. when in skin contact. The ratio of heated area to cooled area is not critical so that a higher fraction of the active area (which includes perimeter 53 and surface 62) may be cooled for better heat management. Improved energy management as well as a decrease of excess heat generation may be accomplished by periodically shutting off the power with the thermoelectric unit open or short circuited during the off time.

In FIG. 6, another alternative embodiment of the somatosensory stimulation device constructed in accordance with the present invention is shown generally at 80. With device 80 head 24' is interchangeable between a strap 86 and handle 22'. An on-off switch 23 is shown on handle 22' for switching the power on and off to head 24'. Head 24' is provided with outwardly projecting protrusions 82 for pivotally attaching the head to a frame 84 which is connected to a longitudinal strap 86 which can be used to strap head 24' to the user's limb for extended usage. Electrical cords 68' and 70' are detachable from head 24' and in use are connected to the power source in handle 22' which in turn may be secured to for example the user's belt by clip 88. An AC adapter 90 is used for recharging the rechargeable power supply. FIG. 7 shows device 80 strapped to a user's arm 92 and FIG. 8 shows the device with the AC adapter 90 coupled to the rechargeable battery in handle 22' in the recharging mode.

In operation, devices 20, 80 or 200 are used for applying heat and cold to adjacent skin areas in the vicinity of pain. The closely adjacent heated and cooled surfaces act to produce enhanced sensory stimulation, the higher the temperature differential providing higher levels of stimulation. The purpose of the present method of alleviating pain is to induce a high degree of somatosensory or neural stimulation in the vicinity of the pain, not to per se heat and/or cool muscles or dilate/contract blood vessels to affect blood flow. The maximum temperature range which can be safely withstood by tissue under prolonged exposure is about 0° to 45° C. without permanent tissue damage. As previously discussed the ratio of hot to cold surface areas is chosen to provide the necessary neural stimulation on the one hand and on the other hand keeping providing heat management or dissipation.

Other patterns of alternating areas to be simultaneously heated and cooled may be used. For example, a checkerboard array of hot and cold sections may be used or alternating concentric rings of both hot and cold strips. The method of the present invention is to provide spatially modulated temperature differentials by the simultaneous application of hot and cold on the skin adjacent to or in the vicinity of pain.

The present invention provides enhanced somatosensory stimulation by concurrently heating and cooling adjacent skin areas in the vicinity of pain to a large but safe temperature differential. The prior methods that employ heat and/or cold sequentially for somatosensory stimulation to block pain are limited because of adaptation or habituation to the sensation. In all these cases the treatments are similar to naturally occurring phenomena and hence the body has built in methods of adaptation. In the present method, large spatially modulated temperature differences within confined areas on the skin surface are generally artificial and accordingly the brain has no mechanism to habituate or adapt other than through total suppression of all signals from stimuli, including pain, from the affected area. Hence, the limitations inherent in sequential heat or cold treatments resulting from habituation or adaptation responses of the brain are reduced.

Put another way, in the method of the present invention the resulting somatosensory stimulation is superior to temporal modulation since the same neural pathways are simultaneously flooded with hot and cold stimulation so the resulting brain response to habituate to the heat causes enhancement of the sensation of cold and conversely habituation to cold serves to increase the sensation of heat, hence any brain response to adapt to one sensation is self-defeating since it causes increased sensitivity to the other. This results in a second order or meta response being triggered in which all sensations from the area, including any pain present, is effectively suppressed. Therefore, assuming that first order adaptation to hot and cold is effectively blocked, then this meta response is triggered.

The term "vicinity" as used herein to describe the application of heat and cold concurrently to the skin in the "vicinity" of pain is used to define that area around the pain locus to which the hot and cold are applied so that the same neural pathways involved with transmitting pain signals are utilized in transmitting the hot and cold signals. Thus as long as the same neural pathways are flooded with hot and cold, the application of hot and cold may not need to be at the pain locus directly.

Similarly, the requirement that the hot and cold be concurrently applied to "adjacent" skin areas is satisfied when such application produces the sensation of a single hot or cold stimulation. This is subjective verification that common neural pathways are receiving both hot and cold stimulation simultaneously since the brain is unable to distinguish the separate sensations or the boundary between them.

Therefore, "adjacent" refers to the amount of separation between the heated and cooled areas necessary to give the aforementioned result so the spacing between areas of hot and cold may vary in a range from being contiguous to a finite separation to give the desired somatosensory stimulation. A temperature differential of 20°–45° C. is preferred.

Figure 9:
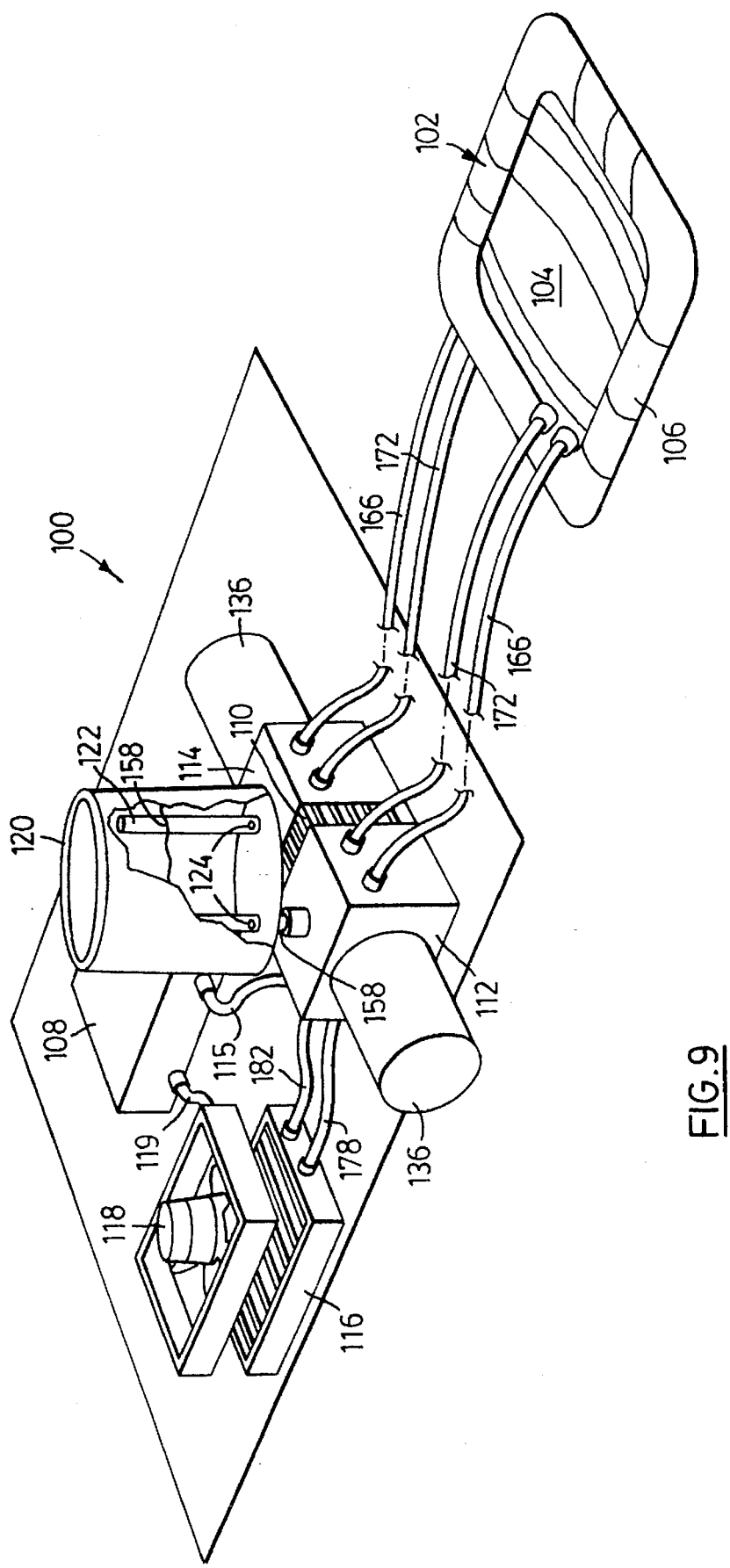
FIG. 9 is a perspective view of another alternative embodiment of an apparatus constructed in accordance with the present invention.

Referring to FIG. 9, another alternate embodiment of a device constructed in accordance with the present invention is shown at 100. Apparatus 100 is a table top plug-in unit which operates with between 50 to 200 watts input power and provides a larger surface area pad 102 having a heated section 104 adjacent to a cooled section 106. A power supply 108 provides power through electrical leads 115 to a thermoelectric unit 110 located between two Identical water pumps 112 and 114. Pump 112 through which the heated water is flowed is in flow communication with a heat exchanger 116 provided with a fan 118 for dissipating excess heat. Power supply 108 provides power to fan 118 through leads 119. Water is supplied to the hot and cold sides from a water tank 120 and a microprocessor (not shown) may be integrated into the system for temperature control.

Figure 10:
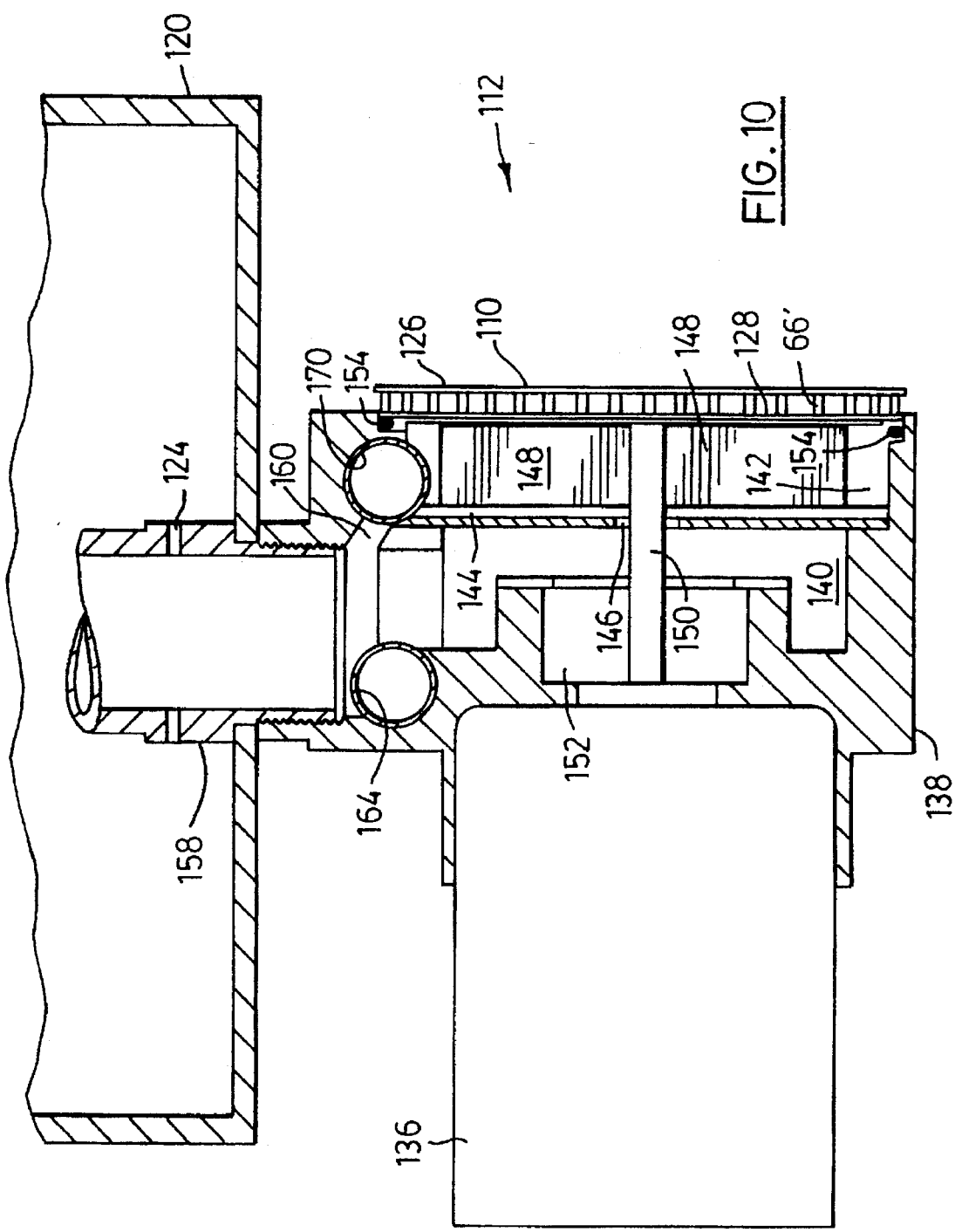
FIG. 10 a sectional view of a water pump forming part of the apparatus of FIG. 9.
Figure 11:
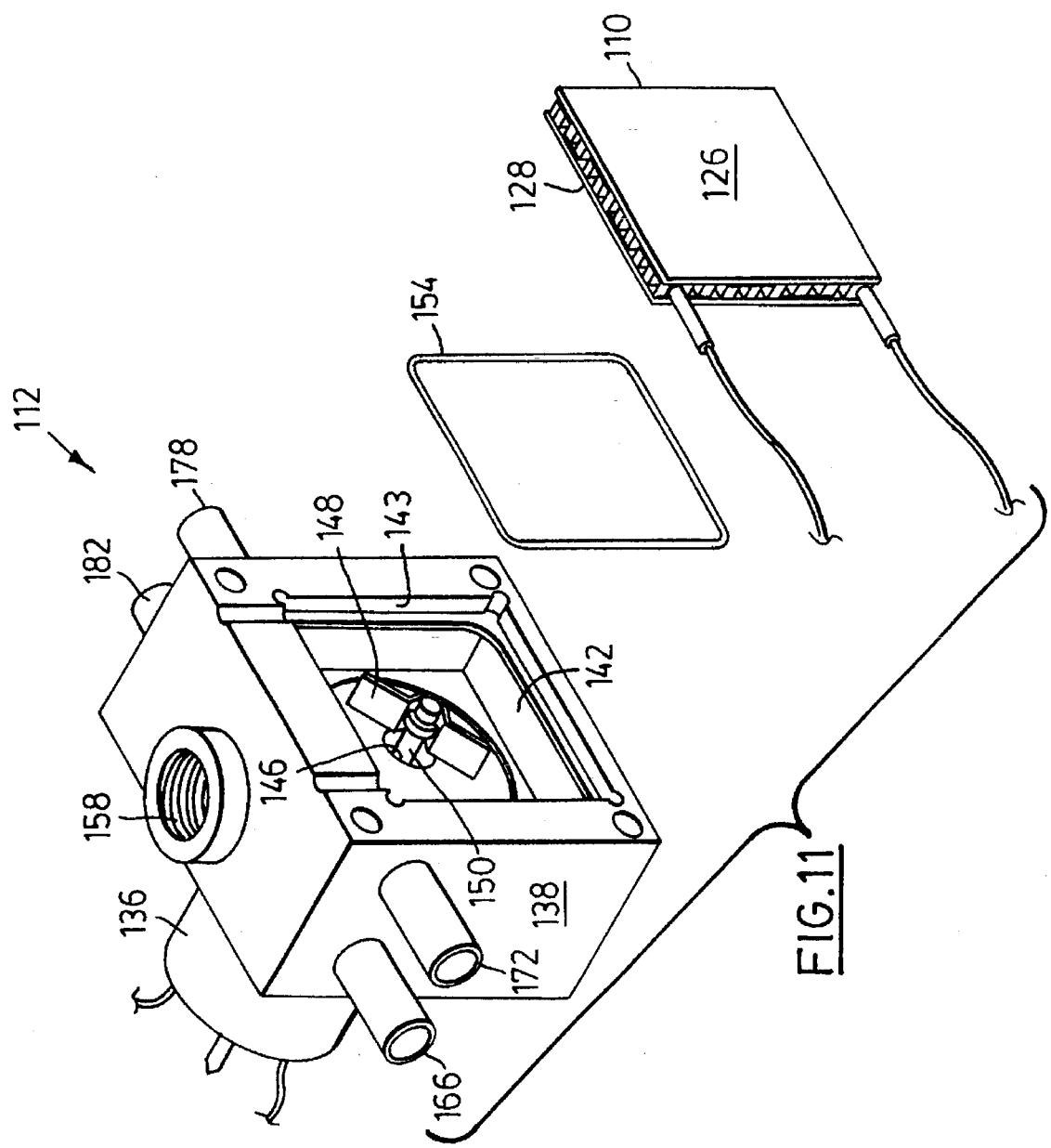
FIG. 11 is an exploded view of a portion of the fluid pump of FIG. 9.

FIGS. 10 and 11 show in greater detail the hot side of the water pump system comprising pump 112 having a motor housing 136, and a housing 138 attached to motor housing 136. Housing 138 defines a first chamber 140 and an impeller enclosure 142. Chamber 140 is separated from impeller enclosure 142 by a disc 144 having a central aperture 146 to provide a fluid flow pathway between chamber 140 and impeller enclosure 142. Housing 138 has an open end portion 143 (FIG. 11) and enclosure 142 and thermoelectric unit 110 is attached to housing 138 at open end portion 143. Side 126 of thermoelectric unit 110 is cooled and side 128 is heated when the current is switched on. Pump 112 includes an impeller 148 mounted for rotation on a motor shaft 150 which passes through a seal 152 into housing 136 where it is operably coupled to the motor.

Impeller 148 is spaced from surface 128 of the thermoelectric unit by about 1 mm, best seen in FIG. 10. An O-ring 154 between thermoelectric unit 110 and housing 138 provides a water seal.

Referring to FIG. 9, the fluid flow system includes a large water inlet tube 158 to introduce water from tank 120 into first chamber 140 in housing 138. This inlet allows for cross-flow exchange of liquid and air but does not provide recirculation. Referring now to FIG. 10, an air escape passageway 160 extending from enclosure 142 to the interior of tube 158 is provided for exhausting trapped air or allowing air to vent out of the pump 112 thereby permitting the system to automatically prime and provide a static pressure on the system. Passageways 164 extend through the side walls of housing 138 which provide fluid flow communication between first chamber 140 and tubes 166 and 182 shown in FIG. 11. Similarly, passageways 170 seen in FIG. 10 extend through the side walls of housing 138 to provide fluid flow communication between impeller enclosure 142 and water outlet tubes 172 and 178 most visible in FIG. 11.

Referring again to FIG. 9, water inlet tubes 158 extend up through the bottom of tank 120 and each has an end portion 122 which is spaced above the water level. Tubes 158 are provided with holes 124 just above the bottom of tank 120, more clearly visible in FIG. 10. Water flows through from tank 120 down through holes 124 into inlet tubes 158 into first chamber 140, through passageway 146 into impeller enclosure 142 and passes over heated/cooled surfaces 128 and 126 respectively of thermoelectric unit 110 and out water outlet tubes 172. This water flow system, comprising inlet tube 158, chamber 140, enclosure 142, air exhaust 160 and recirculation tubes 166, 172, 178 and 182 provides for cross-flow exchange of liquid and air but does not provide for recirculation between tank 120 and the pumps.

When device 100 is assembled as shown in FIG. 9, pump 114 is attached adjacent to side 126 of thermoelectric unit 110 and the pump is essentially identical to pump 112 just described above and water circulated over surface 126 of the thermoelectric unit is cooled except the water does not pass through heat exchanger 116. Tubes 178 and 182 on one side of pump 112 conduct heated water to heat exchanger 116 while for the cooled side with pump 114 the corresponding recirculation tubes (not shown) would not be used. Tubes 166 and 172 on the other side of pump 112 recirculate heated water to and from heated section 104 of water bag 102 and the corresponding tubes on pump 114 recirculate cold water to and from cooled section 106 of water bag 102.

The configuration of pumps 112 and 114 each with an impeller 148 located adjacent to opposite sides of thermoelectric unit 110 is very advantageous in that it provides significantly more efficient heat transfer between the thermoelectric unit and the water compared to previous designs in which the pump is spaced away from the water heater and/or water cooler. By rotating impeller 148 right adjacent to the surface of thermoelectric module 110 provides enhanced heat transfer (fluid shear against the heated/cooled surface) into the fluid thereby increasing the efficiency and cooling power over prior art devices. The centrifugal effect created by the rotating impeller acts to create a pressure differential to give a pumping action useful for mixing the heat transfer liquid and for pumping the fluid through the systems to the components being cooled and heated. Using a single thermoelectric unit 110 to both heat and cool the water with pumps 112 and 114 mounted on either side of the unit provides a more compact system.

In a preferred embodiment of heating and cooling device 100 thermoelectric unit 110 is a Melcor CP 1.4-127-045L or similar device rated at 120 Watts with 15 Volts and 8 amps and a DC motor used to drive impeller 148 operates at 15 Volts below one ampere.

With appropriate selection of power levels and components such as heat exchanger 116 the water heating and cooling may be provided within safe physiological limits without the need for sophisticated and costly temperature and feedback control systems. Flexible pad 102 may be secured to any part of the body using tape, VELCRO™ straps and the like and may be readily deformed to fit the contours of the body. Apparatus 100 may be modified so that the hot and cold sections 104 and 106 of water bag 102 are periodically switched to provide temporal temperature modulation in addition to spatial temperature modulation. This may be done for example by connecting a heat exchanger and fan to pump 114 so that the hot and cold sides of the apparatus are mirror images of each other. Then the hot and cold sides may be rapidly switched by means of a four way ball valve used to redirect and interchange the hot and cold fluid paths.

Another embodiment of the system may be provided which uses air cooling to cool the hot side of unit thermoelectric unit 110 (not shown).

The devices disclosed herein are advantageous for several reasons. All the devices require only one thermoelectric unit to produce both hot and cold. The heat produced as a byproduct of cooling one side of the unit is used to heat the adjacent area using heat exchangers or heat conductors.

Waste heat in excess of that required to heat the skin contacting member is dissipated through forced convection so that this approach considerably reduces the cost of the device and ancillary controls compared to prior art devices.

While the method of alleviating pain using thermally induced somatosensory stimulation has been described and illustrated with respect to the preferred and alternative embodiments, it will be appreciated by those skilled in the art that numerous variations of the invention may be made which still fall within the scope of the invention described herein.

Therefore what is claimed is:

1. A device for simultaneously heating and cooling adjacent skin areas, comprising;
    a) a member adapted to be applied to the skin, said member including at least a first thermally conducting section and at least a second thermally conducting section, said first and second thermally conducting sections being located adjacent to each other for heating and cooling adjacent skin areas; and
    b) means for heating one of said first and second thermally conducting sections to not greater than approximately 45° C. and means for simultaneously cooling the other thermally conducting section to 0° C. or higher, wherein said means for heating and cooling is a thermoelectric unit having first and second surfaces, means for passing a current through said thermoelectric unit to heat one of said first and second surfaces and cool the other.

2. The device according to claim 1 wherein said first thermally conducting section is in thermal contact with said first surface and said second thermally conducting section is in thermal contact with said second surface.

3. The device according to claim 2 including means for releasibly securing said member to the skin.

4. The device according to claim 1 wherein said means for heating and cooling includes a first pump comprising a first housing having an open end portion, said thermoelectric unit being mounted in open communication with said open end portion, said first pump including a motor with a first impeller operably coupled thereto for rotation, the first pump and first impeller being located in said first housing with said first impeller located adjacent to said first surface of the thermoelectric unit, said first housing including at least one first recirculation inlet and first recirculation outlet, whereby in operation rotation of said first impeller forces said heat transfer fluid over said first surface through the first fluid recirculation outlet.

5. The device according to claim 4 including a second pump mounted in open communication with the second surface of the thermoelectric unit, an impeller located in the second housing adjacent to the second surface of the thermoelectric unit, the second housing having a second recirculation inlet and outlet therein, whereby in operation when the impeller is rotated heat transfer fluid is forced over the second surface and out the second fluid recirculation outlet in a second housing.

6. The device according to claim 5 including a flexible bag subdivided into a first bag portion defining said first thermally conducting section and a second bag portion defining said second thermally conducting section, said first bag portion being in fluid flow communication with the first fluid recirculation outlet and first fluid recirculation inlet in the first housing, and the second bag portion being in fluid flow communication with the second fluid recirculation outlet and second fluid recirculation inlet in the second housing.

7. The device according to claim 5 including a heat exchanger in fluid flow communication with said first housing through a recirculation inlet and outlet.

* * * * *